(12) United States Patent
Kim

(10) Patent No.: US 10,311,708 B2
(45) Date of Patent: *Jun. 4, 2019

(54) ALARM AND MONITORING SYSTEM AND METHOD OF OPERATION THEREOF

(71) Applicant: JWIN ELECTRONICS CORP., Port Washington, NY (US)

(72) Inventor: Justin Chiwon Kim, Port Washington, NY (US)

(73) Assignee: jWIN Electronics Corp., Port Washington, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/167,911

(22) Filed: Oct. 23, 2018

(65) Prior Publication Data

US 2019/0057597 A1 Feb. 21, 2019

Related U.S. Application Data

(63) Continuation of application No. 14/937,797, filed on Nov. 10, 2015, now Pat. No. 10,147,305.

(60) Provisional application No. 62/078,460, filed on Nov. 12, 2014.

(51) Int. Cl.
| | |
|---|---|
| *G08B 25/10* | (2006.01) |
| *A61B 5/00* | (2006.01) |
| *H04M 1/725* | (2006.01) |
| *H04M 19/04* | (2006.01) |

(52) U.S. Cl.
CPC .............. *G08B 25/10* (2013.01); *A61B 5/00* (2013.01); *H04M 1/72566* (2013.01); *H04M 19/047* (2013.01); *H04M 1/7253* (2013.01); *H04M 1/72569* (2013.01)

(58) Field of Classification Search
CPC ....... A61B 5/00; G08B 25/10; H04M 19/047; H04M 1/7253; H04M 1/72566; H04M 1/72569

See application file for complete search history.

(56) References Cited

U.S. PATENT DOCUMENTS

| | | | |
|---|---|---|---|
| 5,666,331 A | 9/1997 | Kollin | |
| 6,847,295 B1* | 1/2005 | Taliaferro | G08B 21/0211 340/539.1 |
| 7,336,168 B2 | 2/2008 | Kates | |
| 2005/0141677 A1* | 6/2005 | Hyttinen | H04M 1/72566 379/50 |
| 2006/0273895 A1 | 12/2006 | Kollin | |

(Continued)

*Primary Examiner* — Sisay Yacob
(74) *Attorney, Agent, or Firm* — Mintz Levin Cohn Ferris Glovsky and Popeo, P.C.; Kongsik Kim; Derek E. Constantine

(57) ABSTRACT

An alarm and monitoring system including a primary device and at least one secondary device, the alarm and monitoring system including at least one controller configured to: determine whether at least one alarm event is set; establish a wireless communication between a primary device and the secondary device, when it is determined that the alarm event has been set; transmit an alarm event signal including alarm information from the primary device to the secondary device in accordance with the alarm event that is determined to have been set; generate an alarm signal by the secondary device in accordance with at least the alarm information; and render the generated alarm signal on a rendering device.

20 Claims, 9 Drawing Sheets

(56) References Cited

U.S. PATENT DOCUMENTS

| | | | | |
|---|---|---|---|---|
| 2007/0132562 A1* | 6/2007 | Fukumoto | .......... | B62D 15/0265 |
| | | | | 340/435 |
| 2007/0205887 A1* | 9/2007 | Cho | .................. | G08B 13/1427 |
| | | | | 340/539.15 |
| 2007/0285260 A1* | 12/2007 | Watanabe | .......... | G08B 21/0269 |
| | | | | 340/573.4 |
| 2008/0018459 A1* | 1/2008 | Derrick | .................... | G07C 1/20 |
| | | | | 340/539.13 |
| 2009/0303031 A1* | 12/2009 | Strohallen | .............. | G08B 25/10 |
| | | | | 340/501 |
| 2011/0140868 A1* | 6/2011 | Hovang | .............. | G08B 25/008 |
| | | | | 340/12.55 |
| 2012/0257878 A1* | 10/2012 | Fujimura | ........... | H04N 7/17318 |
| | | | | 386/291 |
| 2012/0329481 A1* | 12/2012 | Malkin | ..................... | G01S 5/02 |
| | | | | 455/456.1 |
| 2013/0234853 A1 | 9/2013 | Kazerouni | | |
| 2014/0031082 A1* | 1/2014 | Zishaan | .................. | G08B 21/12 |
| | | | | 455/556.1 |
| 2015/0052578 A1* | 2/2015 | Yau | ....................... | H04W 12/00 |
| | | | | 726/3 |
| 2015/0061859 A1* | 3/2015 | Matsuoka | .............. | G08B 27/00 |
| | | | | 340/501 |
| 2015/0065095 A1* | 3/2015 | Seo | ..................... | H04L 67/2823 |
| | | | | 455/412.2 |
| 2015/0091723 A1 | 4/2015 | Fiedler | | |
| 2015/0097680 A1 | 4/2015 | Fadell | | |
| 2015/0206421 A1 | 7/2015 | Moffa | | |
| 2015/0332580 A1 | 11/2015 | Bokhary | | |
| 2015/0339913 A1 | 11/2015 | Lyman | | |
| 2016/0072821 A1 | 3/2016 | Wu | | |
| 2016/0085220 A1 | 3/2016 | Yang | | |
| 2016/0272112 A1 | 9/2016 | DeGrazia | | |
| 2017/0006595 A1 | 1/2017 | Zakaria | | |

\* cited by examiner

ALARM AND MONITORING SYSTEM AND METHOD OF OPERATION THEREOF

CROSS-REFERENCE TO RELATED APPLICATIONS

This application is a continuation application of Ser. No. 14/937,797 filed on Nov. 10, 2015, which claims priority to 62/078,460 filed on Nov. 12, 2014. The applications are incorporated herein by reference.

FIELD OF THE PRESENT SYSTEM

The present system relates to an alarm and monitoring system and, more particularly, to an alarm system with sound and/or vibrate mode and/or a monitoring system, which may be controlled by a primary device, such as a smartphone and/or other primary device, and a method of operation thereof.

BACKGROUND OF THE PRESENT SYSTEM

As smart phones become more pervasive, users rely upon an alarm function of the smart phone to generate an audible alarm. Unfortunately, audible alarms have a tendency of waking up more than their intended users. Accordingly, alarms which can vibrate to alert a user have become popular. However, current silent-type alarms must typically be worn by a user to be effective. For example, one common type of silent type alarm must be worn on a wrist of a user. Similarly, monitoring type systems, such as those that monitor sleep, blood pressure, pulse, blood gases, etc., must be worn, which may be of inconvenience to the user. Further, it has been difficult, if not, impossible to customize the prior alarm in accordance with user's settings. Accordingly, embodiments of the present system may overcome these and/or other disadvantages in prior systems.

SUMMARY OF THE PRESENT SYSTEM

The system(s), device(s), method(s), arrangements(s), user interface(s), computer program(s), processes, etc. (hereinafter each of which will be referred to as system, unless the context indicates otherwise), described herein address problems in prior art systems.

In accordance with embodiments of the present system, there is disclosed an alarm and monitoring system including a primary device and at least one secondary device, the alarm and monitoring system including at least one controller that determines whether at least one alarm event has occurred; establishes a wireless communication between a primary device and the secondary device, when it is determined that the alarm event has occurred; generates an alarm event signal including alarm information in accordance with the alarm event that is determined to have occurred; transmits the alarm event signal from the primary device to the secondary device; generates an alarm signal in accordance with at least the alarm information; renders the generated alarm signal on a rendering device of the secondary device. The controller generates the alarm event signal that causes the secondary device to render the generated alarm signal.

In accordance with embodiments of the present system, at least one controller may receive the transmitted alarm event signal at the secondary device which may generate the alarm signal. In operation, the at least one controller may determine capabilities of the secondary device and form the alarm event signal in accordance with the determined capabilities of the secondary device. When generating the alarm signal, the at least one controller may generate the alarm signal in accordance with a selected melody. The secondary device may control one or more other devices to generate the alarm signal. The one or more other devices may include auditory, visual and/or haptic rendering devices to generate the alarm signal.

In accordance with embodiments of the present system, there is disclosed a method of operating an alarm and monitoring system comprising a primary device and at least one secondary device, the method comprising acts performed by at least one controller of determining whether at least one alarm event is set; establishing a communication between a primary device and the secondary device when it is determined that the alarm event has been set; transmitting an alarm event signal including alarm information from the primary device to the secondary device in accordance with the alarm event that is determined to have been set; generating an alarm signal by the secondary device in accordance with at least the alarm information; and rendering the generated alarm signal on a rendering device. The act of establishing the communication may include an act of establishing a wireless communication between the primary and secondary devices. The method may include an act of generating the alarm signal at the secondary device.

In accordance with embodiments of the present system, the method may include an act of determining capabilities of the secondary device. The method may further include an act of forming the alarm event signal in accordance with the determined capabilities of the secondary device. The act of generating the alarm signal may include an act of determining whether communication is established between the primary and secondary devices. When it is determined that communication is established, the method may include an act of providing a user interface in accordance with the determined capabilities of the secondary device. The method may include one or more acts of generating the alarm signal in accordance with rendering information that is stored in a local memory, controlling one or more other devices to generate the alarm signal and the one or more other devices generating at least one of an auditory, visual and haptic alarm signal.

BRIEF DESCRIPTION OF THE DRAWINGS

The present invention is explained in further detail in the following exemplary embodiments and with reference to the figures, where identical or similar elements may be partly indicated by the same or similar reference numerals, and the features of various exemplary embodiments being combinable. In the drawings.

DETAILED DESCRIPTION OF THE PRESENT SYSTEM

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well-known devices, circuits, tools, techniques, and methods are omitted so as not to obscure the description of the present system. It should be expressly understood that the drawings are included for illustrative purposes and do not represent the entire scope of the present system. In the accompanying drawings, like reference numbers in different drawings may designate similar elements.

The present system as described in more detail below may provide for a primary device that utilizes a user interface to enable setup and programming of a secondary device. In accordance with embodiments of the present system, the primary device may operate as a master device to the secondary device which in these embodiments operates as a slave device (e.g., master/slave relationship between devices). Other relationships between devices may be suitably utilized in accordance with embodiments of the present system and are intended to be encompassed by the simplified following discussion.

In operation the primary device may transfer alarm information to the secondary device that at an alarm time, may operate as an alarm device with sound and/or vibrate mode. Further, the secondary device may operate, such as using a wireless connection, to control other devices such as a haptic device (e.g., vibrating), light source (e.g., lamp turn on, gradually brighten and/or flashing) and/or speaker (e.g., render audio) for rendering the alarm. Further, the secondary device may operate to control other devices such as a haptic, visual, auditory, and/or environmental device such as a thermostat for example to respond to the alarm information such as to adjust an environment based on the alarm information (e.g., warm a room before a wake-up alarm is generated).

Figure 1A:
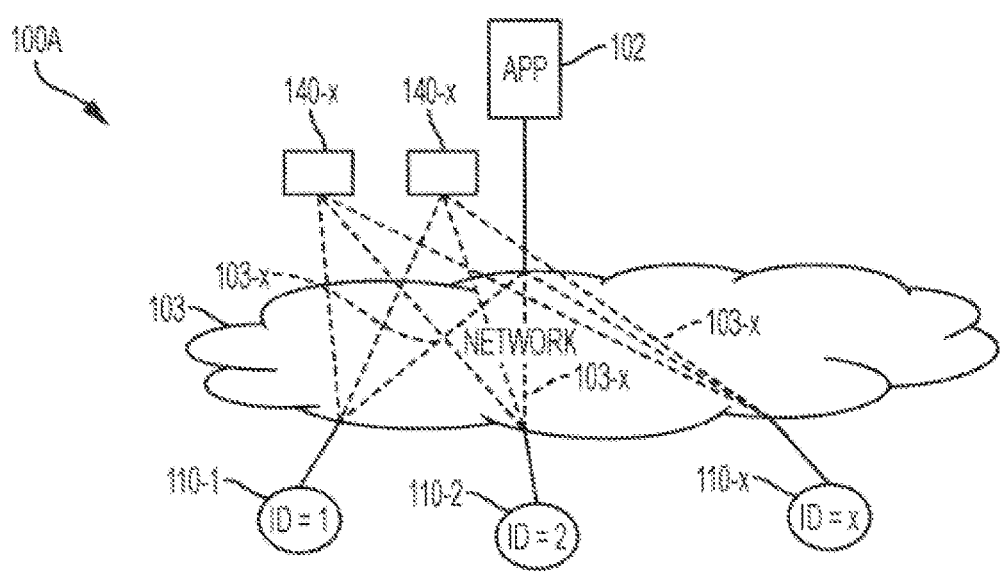
FIG. 1A shows a block diagram of a portion of an alarm and monitoring system in accordance with embodiments of the present system.

FIG. 1A shows a block diagram of a portion of an alarm and monitoring system (hereinafter system for the sake of clarity) 100A in accordance with embodiments of the present system. The system 100A may include a device 102 (which may be referred to herein as a primary device) and one or more secondary devices illustratively shown as secondary devices 110-1 through 110-P (generally secondary device 110-x).

The primary device 102 and the secondary device 110-x may communicate with each other over any suitable connection such as over the network 103 which may be accessed using wired and/or wireless communication links. For example, the primary device 102 and the secondary device 110-x may communicate over a network 103 using any suitable wireless, at least in part, communication method or protocols such as WiFi™, Bluetooth™, Internet Protocol, or the like. In addition or in place of a network-based communication, in accordance with embodiments of the present system, a partial hardwired communication connection, such as a home wired network, a direct wired connection, such as through a direct cable connection, and/or a direct wireless communication, such as one or more connections 103-x, such as Bluetooth™, etc., is also envisioned. The discussion of the network, such as the network 103 herein should be understood to include any one or more of the communication systems and/or others that may be suitably applied. For example, in accordance with an embodiment, the primary device may communicate with the secondary device over a Bluetooth™ connection while the secondary device communicates with another device (e.g., one or more other devices 140-x) using a WiFi™ connection. As appreciated, the same or different connections may be made between various devices which may also vary over time (e.g., WiFi™ connection at one time and Bluetooth™ connection at another time).

Further, one or more of the secondary devices 110-x may operate, such as using a wireless connection (e.g., network 103), to control the one or more other devices 140-x, such as a haptic device (e.g., vibrating), light device (e.g., lamp turn on, gradually brighten and/or flashing), speaker (e.g., render audio) and/or other device (e.g., a thermostat) for rendering the alarm information and/or otherwise responding. In accordance with embodiments of the present system, one or more of the rendering devices may be a portion of the secondary device such that the secondary device and/or the other device may respond to the alarm information.

In accordance with embodiments of the present system, the primary device 102 may include any suitable communication device such as smartphone (e.g., an IPhone™, etc.), laptop, tablet, etc., and may run one or more applications to provide functionality as described herein. However, it is also envisioned that the primary device 102 may include additional communication devices such as a dedicated alarm communication device and/or processor operating in accordance with embodiments of the present system.

With regard to the secondary device 110-x, each of these devices may include a unique identification (ID) which may be used to identify and/or otherwise communicate with the corresponding secondary device 110-x, as desired. With regard to the secondary devices 110-x, one or more of these devices may for example be similar to and/or differ (e.g., provide a different form and/or function) from each other and/or from the illustrative discussion herein. However, for the sake of clarity, only a single secondary device 110 is generally illustratively discussed unless the context indicates otherwise.

Figure 1B:
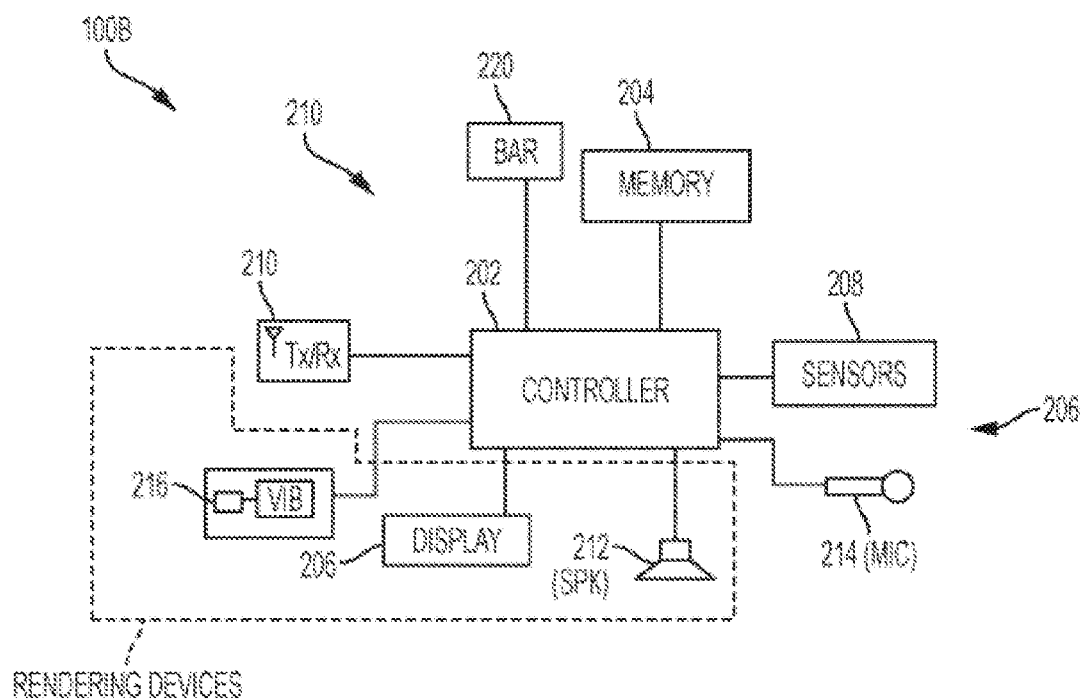
FIG. 1B shows block diagram of a device operating in accordance with embodiments of the present system.

FIG. 1B shows block diagram 100B of a secondary device 210 operating in accordance with embodiments of the present system. The secondary device 210 may, for example, be similar to the secondary device 110 and may include one or more of a controller 202, a memory 204, one or more rendering devices, such as a display 206, a speaker (SPK) 212, and/or a haptic device such as a vibrator 216, a microphone (MIC) 214, a transmit/receive (Tx/Rx) portion 218, and/or one or more sensors 208, one or more of which may communicate with each other and/or to the controller 202. Power for the secondary device 210 may be provided by a power storage device 220 such as a battery. While each of the components of the secondary device 210 are separately depicted, it is envisioned that two or more of the components may also be integrated together. For example, the controller 202 may include a microprocessor and the transmit/receive (Tx/Rx) portion 218. Further, one or more of the rendering devices, such as one or more of the display 206, the speaker (SPK) 212, and/or the haptic device 216 may also or in place of being enclosed with the secondary device 210, be provided separate from the secondary device 210 yet be controlled (e.g., wirelessly) to operate as described herein such as one or more of the other devices 140-x (e.g., haptic device, light device, speaker, thermostat, etc.) illustratively shown in FIG. 1A. For example, the secondary device 210 may control other devices wirelessly, such as a heating/ventilation thermostat and/or other system to control the other system to respond (e.g., adjust heating/ventilation) to the alarm information as described herein. The controller 202 suitably configured may control the overall operation of the secondary device 210 and may include one or more logic devices such as switches, gates, micro-controllers, processors (e.g., micro-processors, etc.) and/or the like to process information in accordance with embodiments of the present system. The memory 204 may include any suitable memory such as local and/or distributed memory which may store application programs (e.g., Mobile Applications, etc.), user information (e.g., user settings, etc.), system settings, etc. The memory 204 may include a local and/or distributed memories, as desired. In accordance with embodiments of the present system, the memory 204 may store software such as applications which may configure the controller 202 to operate as a special purpose controller and/or processor in accordance with embodiments of the present system. In accordance with embodiments of the present system, the memory 204 may include non-transitory memory.

The Tx/Rx portion 218 may receive information from the controller 202 for transmission via any suitable wireless and/or wired system as described herein, via the antenna (ANT) and/or may receive information from any suitable wireless and/or wired system such as the antenna (ANT) and provide this information to the controller 202. The Tx/Rx portion 218 may for example further up convert and/or down convert information as may be suitable for operation as configured. In accordance with embodiments of the present system, the Tx/Rx portion 218 may communicate via any suitable communication method such as via a wireless network, and/or other network as described. In accordance with embodiments of the present system, the Tx/Rx portion 218 may communicate for example using any suitable communication protocol and/or system such as via WiFi™ and/or Bluetooth™ systems.

The one or more rendering devices including one or more of a visual, auditory and/or haptic rendering device may be a portion of the secondary device 210 and/or may be housed in an enclosure separate from the secondary device 210. In embodiments where there are one or more separate rendering devices, the controller 202 may communicate with the separate rendering devices for example utilizing the Tx/Rx portion 218. The one or more rendering devices may operate to provide a user interface UI 206 that may include a display (DISP) (e.g., a touch-screen display) or the like which may render information such as a graphical user interface (GUI) for operation in accordance with embodiments of the present system. For example, the controller 202 may form a user interface (UI) such as a GUI and provide the GUI to the display for rendering in accordance with embodiments of the present system. Further, in accordance with embodiments of the present system the user interface (UI) 206 may provide illumination sources such as one or more light emitting diodes (LEDs) which may be lit individually and/or collectively (e.g., two or more) to indicate information for the convenience of the user. Operation of the rendering devices contained herein is understood to apply whether the rendering device is provided as a portion of the secondary device 210 or is enclosed separate from it.

In accordance with embodiments wherein the UI 206 includes an auditory portion, a speaker 212 may include one or more speakers which may render audio information, for example obtained from the controller 202, the memory 204, the Tx/Rx portion 218, etc., for the user. For example, the speaker 212 may provide auditory information to a user, such as an auditory alarm, sounds to facilitate relaxation (nature sounds, music, etc.), sleep, etc., under control of the controller 202. Similarly, the haptic device 216 may provide haptic information to a user, such as a haptic alarm, etc., under control of the controller 202. Such haptic and/or auditory information may be pre-stored locally in the memory and/or may be transmitted to the device 210-x in a suitable format prior to being rendered, such at the time of interaction with the primary device. In an embodiment wherein the haptic and/or auditory device are provided separate from the secondary device 210, the secondary device 210 may control (e.g., using a Bluetooth™ communication link) the separate haptic and/or auditory device to activate at the time of an alarm.

In an embodiment wherein the haptic and/or auditory device is operated to notify, awaken, or otherwise alert the user, the haptic device and/or speaker may render related information at a fixed and/or ascending (e.g., periodically increasing) level as programmed and/or otherwise set, desired, etc. For example, in an embodiment wherein an ascending haptic and/or auditory level is produced, the haptic and/or auditory level may start at a first level for a period of time, which in an event wherein the user does not operate to stop rendering, the controller may operate periodically to increase the haptic and/or auditory level to higher levels until a maximum level is reached or the user operates to stop the rendering. Similarly, in an embodiment wherein a descending haptic and/or auditory level is produced, the haptic and/or auditory level may start at a first level for a period of time, which in an event wherein the user does not operate to stop rendering, the controller may operate periodically to decrease the haptic and/or auditory level to lower levels until a minimum level is reached or the user operates to stop the rendering. In accordance with embodiments of the present system, the controller may operate through programming and/or construction to produce a fixed haptic and/or auditory level until the user operates to stop the rendering. The system may produce a corresponding haptic and/or auditory level for a period of time, at which time, the controller may operate to stop the rendering without user intervention.

In accordance with embodiments of the present system, the MIC 214 may acquire ambient sound and form corresponding audio information which may then be provided to the controller 202 for further processing. For example, the MIC 214 may detect ambient sounds such as sounds formed by a user (e.g., such as voice commands, sleeping sounds, etc.) and may correspondingly provide audio information to the controller 202 for storage, transmittal, and/or further processing. For example, the controller 202 after receipt may then further process this audio information and may transmit the audio information to the primary device (e.g., 100, FIG. 1A) for further processing. In accordance with embodiments of the present system, the controller 202 may store the audio in the memory 204 for later use, such as for later transmission, as desired, programmed, etc.

In accordance with embodiments of the present system, the MIC 214 may acquire sounds such as voice commands (requests), sleeping sounds, etc., from a user. The sounds may be received by the controller 202 which may store and/or transmit these sounds (e.g., voice commands) as raw and/or processed information to the primary device (e.g., 100, FIG. 1A) which may then process these sounds (e.g., using speech-to-text (STT) processing) for example to identify the sounds and take appropriate action. In accordance with embodiments of the present system, a user may, for example, provide a voice command, such as request a snooze operation of an alarm, answer a call, hang up on a call, create a text message, read or send a text message, etc. For example, the MIC 214 may acquire audio information which may for example be used by the controller 202 to initiate and/or terminate hands-free phone calls. In accordance with embodiments of the present system, the MIC 214 may be included as one of the sensors 208. Further, the present system may provide a hands-free functionality for the user by the secondary device 210 operating with the primary device (e.g., primary device 102) in accordance with embodiments of the present system. Further, the secondary device of the present system may acquire sleeping sounds for processing by or together with the primary device (e.g., primary device 102) in accordance with embodiments of the present system for example to enable sleep analysis and/or sleep recommendations.

The one or more sensors 208 may include one or more sensors which may detect sound, light, touch, temperature, humidity, pressure, orientation, motion, and/or acceleration and form corresponding sensor information including temporal data related to the sensor information (e.g., periodic sensor information and a time of the periodic sensor information) for example, to enable sleep analysis as described herein. For example, temporal sensor information may be utilized to determine an environment (e.g., sound, light, temperature, humidity and ambient pressure) of a user during sleep as well as the user response (e.g., snoring, motion, etc.) to the environment.

Further, in accordance with embodiments of the present system, touch sensors may include hard and/or soft switches/sensors which may for example detect motion, touch, etc., and form corresponding sensor information. The motion and/or acceleration sensors may detect motion and/or acceleration in (or along) one or more axes and may form corresponding sensor information (e.g. acceleration information). For example, in accordance with embodiments of the present system one or more acceleration sensors may form acceleration information corresponding to one or more axis. In accordance with embodiments of the present system, a drop sensor may be provided to detect a fall and form corresponding information.

In accordance with embodiments of the present system, orientation sensors may detect an orientation of the secondary device 210 and form corresponding orientation information. For example, in accordance with embodiments of the present system, the orientation sensors may detect a right-side or upside down orientation of the secondary device 210 and form corresponding information. In embodiments, it is envisioned that the orientation sensor(s) may detect an orientation of the secondary device 210 relative to a fixed orientation such as magnetic north and form corresponding sensor information (e.g., orientation information). For example, the sensor(s) may collect information related to a user's sleep habits (e.g., sounds, motion, etc.) and form corresponding sensor information which may then be transmitted to the primary device (e.g., primary device 102) for further processing by its controller, such as to provide recommendations to the user related to the sleep habits as described herein. For example, in embodiments wherein the secondary device 210 in positioned to monitor a user's sleep habits (e.g., positioned under a pillow and/or otherwise positioned, fastened, etc. with relation to a pillow, mattress, etc., of a user), the motion sensor(s) may collect (e.g., store) and/or transmit motion information to the primary device which may then be utilized to determine/track sleep quality using this information as discussed.

The haptic device 216 may include any suitable haptic device which may render haptic information. For example, in accordance with embodiments of the present system, the haptic device 216 may include any suitable vibrator (VIB) (e.g., a rotational or linear motor with an unbalanced mass) that may generate vibration which may be sensed by a user. The haptic device may be shaped, sized, and/or powered, etc., such that it may generate sufficient vibration to notify, wake, etc., a user even when placed, for example, under a pillow or the like. In accordance with embodiments of the present system, the VIB may be driven using a signal which may have a uniform, periodic (e.g., sinusoidal, etc.), and/or non-periodic drive signal so that, for example, the vibration may vary in accordance with the drive signal. The power device 220 may include any suitable power storage device which may store power such as a battery, a capacitor, and/or the like.

Figure 2A:
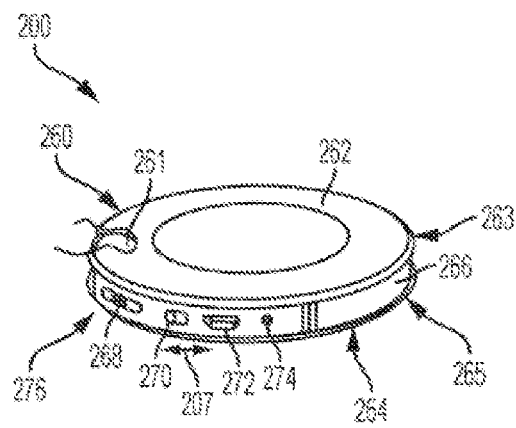
FIG. 2A shows a partially cutaway top front perspective view illustration of a portion of a device in accordance with embodiments of the present system.

FIG. 2A shows a partially cutaway top front perspective view illustration of a portion of a device 200, such as a device 210-x (e.g., illustratively a secondary device), in accordance with embodiments of the present system. As readily appreciated, the device may take other forms including a form that may be fastened to a pillow, mattress, etc., of a user, etc. Any of these suitable forms are encompassed by the description herein. As described, one or more of the components, such as the rendering devices may be provided separate from the secondary device 200, yet still be operated as described herein. The secondary device 200 may for example be similar to the secondary device 110, 210 and may include a formed body 260 for example having an upper housing 262, a lower housing 264, a middle housing 266, and/or an interface portion 276. For example, the body 260 may define an interior cavity 261 and may contain one or more components in accordance with embodiments of the present system. The interface portion 276 may include one or more switches, connection ports for communicating with the secondary device 200, and/or a rendering device, such as a display (e.g., one or more light-emitting diodes (LEDs)), etc. For example, in accordance with embodiments of the present system, the interface portion 276 may include one or more switches, buttons, etc., (e.g., a button 268), such as a snooze button, a stop button (e.g., to stop rendering), a power switch 270, a battery charging port 272, and/or one or more MIC 274. As readily appreciated, any one or more of the switches, buttons, etc., may perform one or more operations in accordance with embodiments of the present system. For example, in one mode a button may operate as a snooze button to temporarily stop the rendering of an alarm while in a separate mode, such as during the establishment of a communication link, the button may operate to initiate the communication link.

The switches such as the button 268 and/or the power switch 270 may be situated for example around a periphery of the housing 266 so as to be shielded from accidental activation. However, in yet other embodiments, it is envisioned that one or more of the buttons, switches, etc., may be located elsewhere such as on one or more of the upper and lower housing 262 and 264, respectively. However, a cover such as a hinged cover, a locking mechanism, or other type of shielding (e.g., a wire protector) may be provided to shield one or more of the buttons, switches, etc., from accidental activation, intrusion, etc.

In accordance with embodiments of the present system, the button 268 and/or the power switch 270 may include any suitable switch type such as hard (e.g., pushbutton-type, slide-type, toggle-type) and/or soft (e.g., touch-sensitive-type, programmable, alterable display or indication of operation, etc.) switch of one or more types. For example, it is envisioned that the button 268 and/or the power switch 270 may be formed using one or more hard and/or soft type switches such as touch-sensitive-type switches. Further, in accordance with embodiments of the present system, a snooze and/or power operation may include one or more switches (e.g., a combination of switches actuated simultaneously and/or in sequence, such as press switch key 1 and key 2 together for snooze, etc.). In accordance with embodiments of the present system wherein more than one switch/sensor is utilized for an operation, this combination may be assigned by default, by the user by the system and/or otherwise programmed.

The power switch 270 may be for example hard-type switch such as a slide-type switch which may be activated (e.g., switched on) and/or deactivated (e.g., switched off) by sliding as illustrated by arrow 207. When, the power switch 270 is placed in the "on" position, the secondary-device 200 may be turned on for operation in accordance with the present system. When, the power switch 270 is placed in the "off" position, the secondary-device 200 may be turned off or otherwise be placed in an inactive state, such as in a low-power or no power usage state.

In accordance with embodiments of the present system, the button 268 may include a press-type switch and may generate for example a snooze signal which may be transmitted to a primary-device (e.g., primary device 102) for further processing. For example, depressing a snooze button may cause the primary device to suspend a rendering, such as an auditory alarm, for example for a period of time (e.g., 5 minutes, etc.). In accordance with embodiments of the present system, each time the button 268 is depressed, a controller of the system may extend (e.g., stack, add or otherwise extend a current delay time) and/or otherwise provide a delay time until the next alarm by a desired period of time such as 5 minutes, etc., as may be set by default, by the system, by a user and/or otherwise programmed.

The battery charging port 272 may include any suitable port for receiving a cable and/or device such as a universal-serial bus (USB)-type port or the like to provide power to the secondary device 200. However, in accordance with embodiments of the present system, it is envisioned that other types of ports and/or a wireless charge port may be provided, for example to wirelessly provide power to charge a battery and/or otherwise provide power to the secondary device 200. In accordance with embodiments of the present system, the port 272 may also operate as the transmit/receive (Tx/Rx) portion, such as the transmit/receive (Tx/Rx) portion 218, for transmitting and/or receiving programming instructions, such as alarm settings, monitoring settings, melodies, etc., as described herein.

Figure 2B:
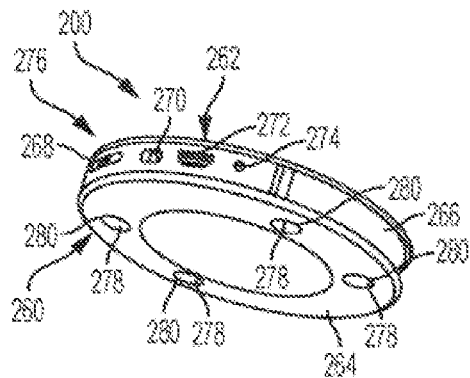
FIG. 2B shows a bottom front perspective view of a portion of a device in accordance with embodiments of the present system.

FIG. 2B shows a bottom front perspective view of a portion of the secondary device 200 in accordance with embodiments of the present system. Caps 278 may be mounted within openings 280 that are configured to receive securing devices such as screws. The caps 278 may fit flush or may extend slightly past an exterior periphery of the lower housing 264 so as to act as mounting pads or cushions.

Figure 3A:
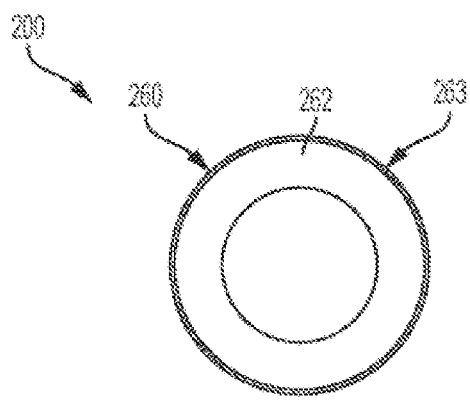
FIG. 3A shows a top planar view of a portion of a device in accordance with embodiments of the present system.

FIG. 3A shows a top planar view of a portion of the secondary device 200 in accordance with embodiments of the present system. As previously discussed, the body 260 may have any desired shape such as a round shape, ovoid, and/or partial ovoid. However, in accordance with embodiments of the present system other shapes are also envisioned as described herein. The upper housing 262 may have an outer peripheral rim 263 which extends slightly past an outer periphery of the middle housing 266 to protect for example the interface 276 or portions thereof such as switches from unintended activation such as due to accidental contact. Accordingly, the outer peripheral rim 263 may protect the interface 276 and portions thereof from for example accidental impact if, for example, the secondary device 200 is dropped unto a hard surface (e.g., a desktop, a floor, etc.) or is placed under a pillow.

Figure 3B:
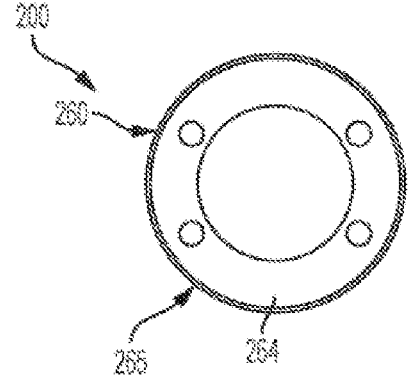
FIG. 3B shows a bottom planar view of a portion of a device in accordance with embodiments of the present system.

FIG. 3B shows a bottom planar view of a portion of the secondary device 200 in accordance with embodiments of the present system. The lower housing 264 may have an outer peripheral rim 265 which extends slightly past an outer periphery of the middle housing 266 for example to protect the interface 276 from unintended contact. The outer peripheries 263 and 265 of the upper and lower housings 2652 and 264, respectively, may be the same as (e.g., in shape and/or size) or different from each other and may cooperate as described herein.

Figure 3C:
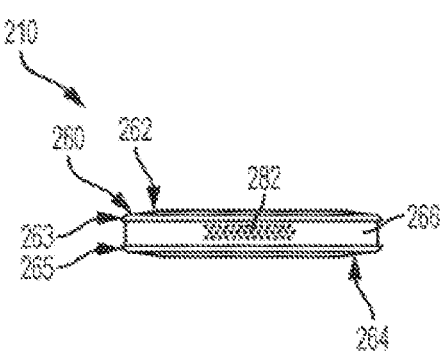
FIG. 3C shows a rear planar view of a portion of a device in accordance with embodiments of the present system.

FIG. 3C shows a rear planar view of a portion of the secondary device 200 in accordance with embodiments of the present system. The middle housing 268 may include patterns and/or vents 282 to promote ventilation (e.g., cooling) and/or allow exiting of for example audio emissions (e.g., generated by a rendering by the speaker such as the SPK 212) from an interior cavity of the secondary device 200.

Figure 4:
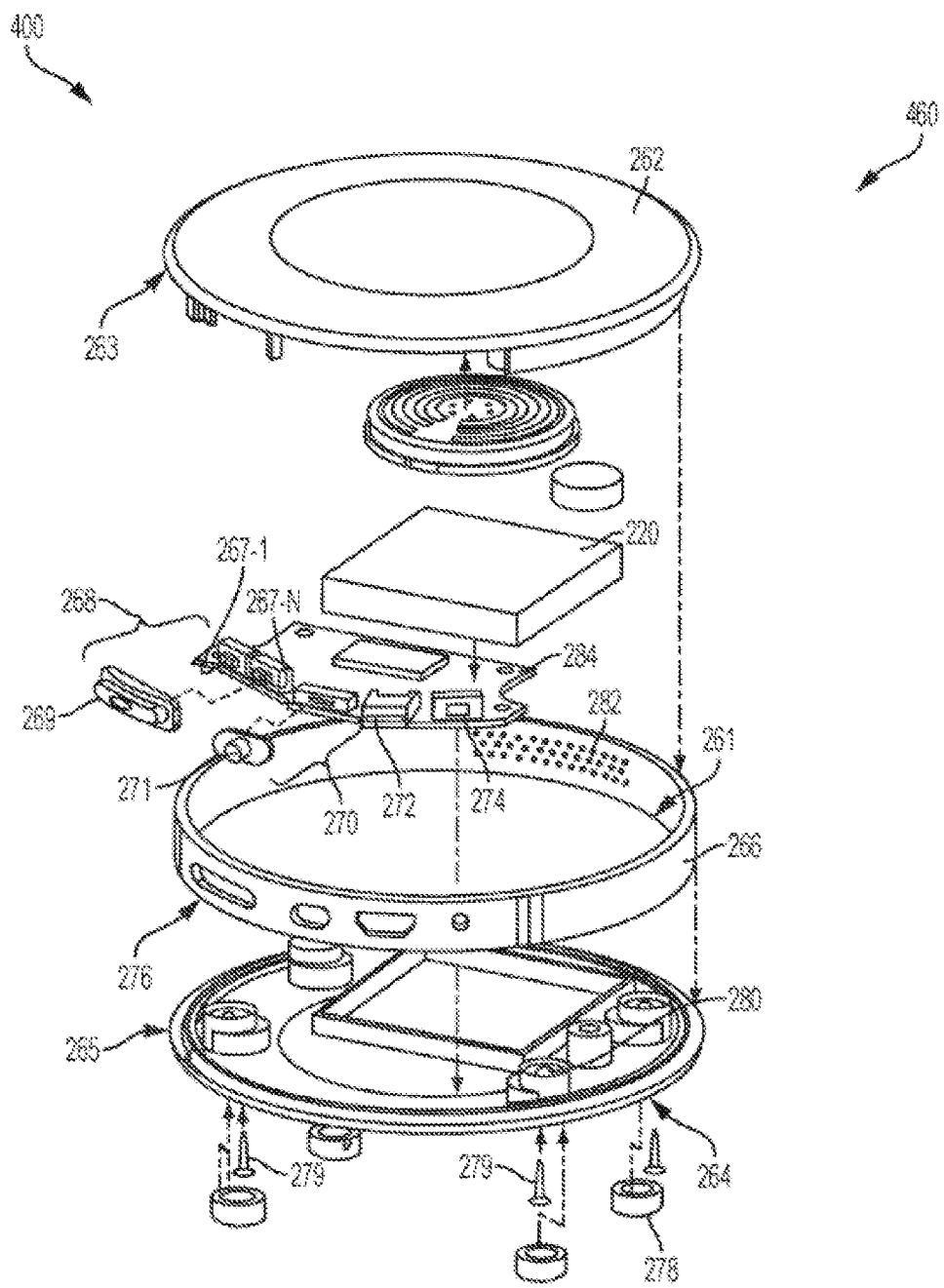
FIG. 4 shows a partially exploded front perspective view of a device in accordance with embodiments of the present system.

FIG. 4 shows a partially exploded front perspective view of a device 400 in accordance with embodiments of the present system. As discussed, the device may operate as a secondary device that may for example be similar to the secondary device 200 and may include a body 460 which is illustratively shown as similar to the body 260. The body 460 may enclose one or more of the components of the present system, such as the rendering devices however, as described, one or more of these components may also or alternatively be enclosed separate from the body 460.

Accordingly, similar numerical designations may be used to designate the same or similar portions. However, it should be understood that these portions may, in accordance with embodiments of the present system, differ from those of the secondary device 200.

As discussed, the button 268 may operate as a snooze button and may be a hard-type switch including a cover portion 269 and one or more actuators such as press-type switches 267-1 and 267-N (generally 267-x) thus forming a combination switch which may be pressed singularly for corresponding functions and/or may be pressed in unison (e.g., two or more switches being depressed simultaneously and/or in sequence) for another function. For example, these functions and/or actuations may be assigned by default, by the system, by a user and/or may be otherwise programmed. The power switch 270 may include a cover 271 coupled thereto and with which a user may interact to move (e.g., by sliding, etc.) the power switch 270 to on or off positions.

An interface board 284 may be situated within the cavity 261 of the body 260 and may be coupled to and/or may couple together one or more of the snooze button 268, the power switch 270, the battery charging port 272, and the MIC 274. The middle housing 266 may include one or more openings through which one or more of the snooze button 268, the power switch 270, the battery charging port 272, and the MIC 274 may pass and/or be accessed. The speaker 238 and/or the vibrator 246 may be situated adjacent to the upper housing 262 and/or may be housed separate from the body 460 as described. A coupler such as screws 279 (or other suitable coupling method such as welding, friction fitting, etc.) may couple the upper housing 262 to the lower housing 264 so as to sandwich the middle housing 266 therebetween. Accordingly, the screws 279 may pass through openings 280 which are situated within the lower housing 264. Caps 278 may then be frictionally fit within at least a portion of the openings 280 so as to conceal the screws 279. The power storage device 220 may include any suitable power storage device which may provide power such as a rechargeable battery and/or a capacitor and may receive a charge for example from the battery charging port 272.

Figure 5:
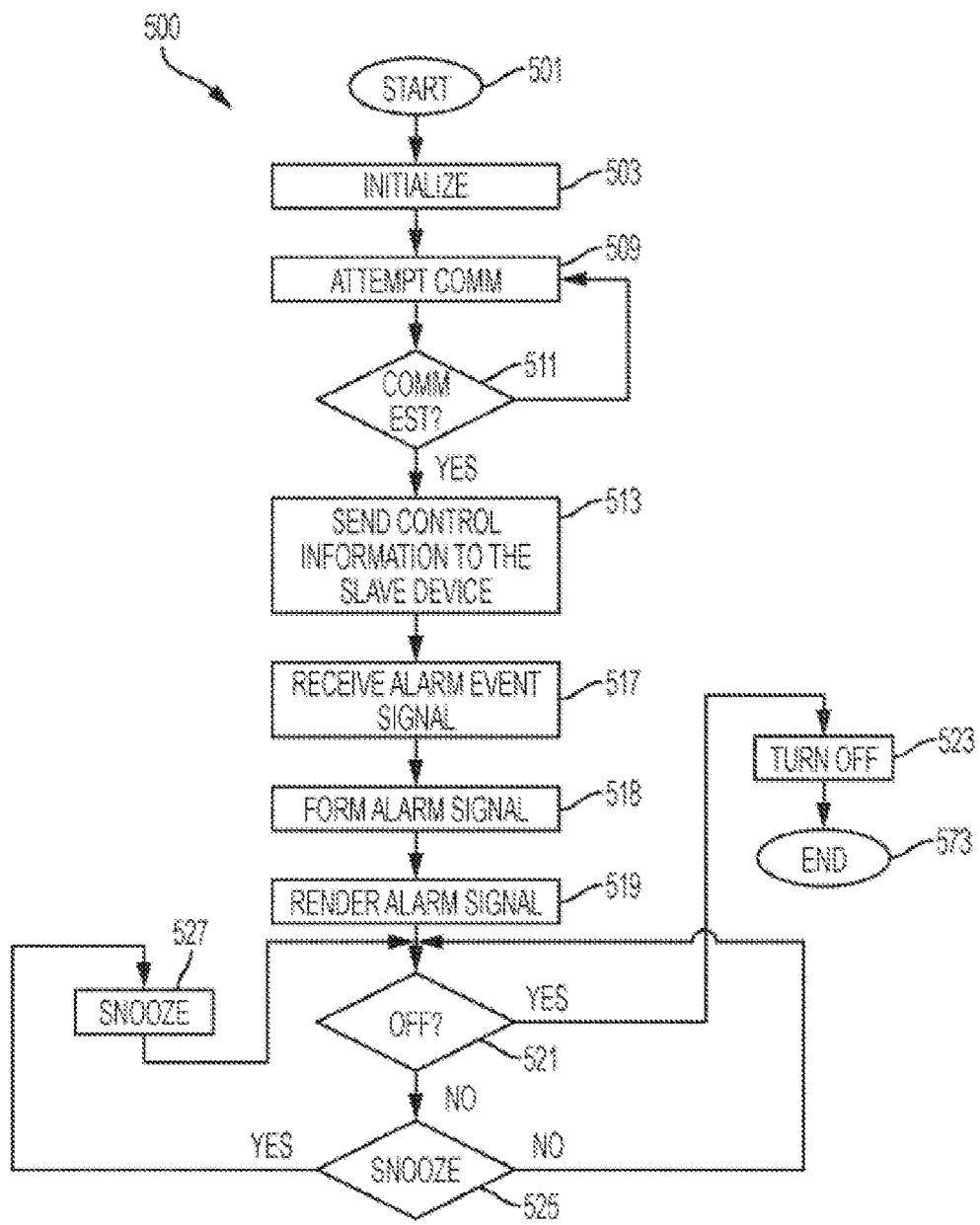
FIG. 5 shows a functional flow diagram of a portion of a process performed in accordance with embodiments of the present system.

FIG. 5 shows a functional flow diagram of a portion of a process 500 performed in accordance with embodiments of the present system. The process 500 may be performed using one or more computers communicating over a network and may obtain information from, and/or store information to one or more memories which may be local and/or remote from each other. The process 500 may include one of more of the following acts. In embodiments of the present system, the acts of process 500 may be performed using one or more alarm systems operating in accordance with embodiments of the present system. Further, one or more of these acts may be combined and/or separated into sub-acts, if desired. Further, one or more of these acts may be skipped depending upon for example settings, embodiments, etc. In operation, the process may start during act 501 and then proceed to act 503.

During act 503, the user may for example download a corresponding application to a primary device, such as a smartphone. In accordance with embodiments of the present system, the Application may include programming portions that configure the primary device for operation as described herein such as by providing a user interface as described. Thereafter, the primary may attempt to form a communication link with the secondary device during act 509 to enable further operation. For example, in a case wherein a Bluetooth™ communication link is utilized, turning on the secondary device may cause the secondary device to be discoverable on the smartphone. Thereafter the primary and secondary devices may attempt to communicate together (e.g., may attempt pairing by a Bluetooth™ communication link) during act 511 over any suitable connection and/or method. For example, in accordance with embodiments of the present system, a Bluetooth™ connection may be established (e.g., pairing) between the primary device and the selected secondary device. In accordance with embodiments of the present system, a user may select a preferred type of communication method (e.g., WiFi™, Bluetooth™, Zig-Bee™, proprietary, RFID, etc.) for communication when more than one system of communication is available between the devices. In accordance with embodiments of the present system, other operations may be utilized for initiating the communication link such as depressing a button on the secondary device to initiate a communication link with the primary device.

In an embodiment wherein one or more secondary devices are available, a communication link may be attempted between the primary device and the one or more available secondary devices. In accordance with embodiments of the present system, each device (e.g., primary and/or secondary devices) may have a unique identification (ID) (e.g., a unique identification). Thus, in accordance with embodiments of the present system, for example each secondary device may be assigned a unique number from 1 to P in a case wherein more than one secondary device is available. However, to simplify the discussion, only a primary and single secondary device (e.g., p=1) is discussed, for example having an ID of ID=1 for the sake of clarity.

After the communication link is confirmed between the primary device and the secondary device during act 511, the user may open the application to enable operation in accordance with the present system. For example, the application may be utilized to set the device (e.g., a secondary device 110-x) to operate in accordance with the present system as well as depicting on the primary device an operating state (e.g., communication link status such as connected, battery status, operating mode such as alarm, sleep monitoring, etc.) of the secondary device. In a case wherein the communication link is not confirmed, the process may continue to attempt communication (e.g., repeat act 509) until a communication link is established during act 509 and/or may return to act 503 for further configuration operations.

In a case wherein the communication link is established, the application on the primary device may be utilized for sending control information to the secondary device during act 513 such as to set an operating mode of the secondary device. In accordance with embodiments of the present system, the control information may include alarm information (e.g., date, time, alarm type, rendering device, etc.), operating mode information (e.g., sleep monitoring), rendering information, etc. For example, the process may configure alarm settings and/or alarm times (e.g., by date, day, time, etc.) for one or more alarm events. In operation, a user may set an alarm within the application on the primary device for a time (e.g., every Tuesday, this Tuesday, etc.) for a given alarm event and transmit this information to a memory of the system, such as within the secondary device, as alarm information during act 513 for later use (e.g., "later" as in at the time of a given alarm) by the secondary device. In this way, there is no need for the primary and secondary devices to have an operable communication link at the time when a given operating mode is intended (e.g., see act 519) such as at a given alarm time for the secondary device to produce the given alarm and/or to control external devices (e.g., other devices, such as a light, speaker, haptic device, thermostat, coffee maker, etc.) to perform an operation at the given alarm time and/or at a time related to the alarm time. For example, in accordance with embodiments of the present system, the secondary device may communicate with another device, such as a lamp, to increase a light brightness for example in intervals producing an increasing amount of light leading up to the alarm time. In other embodiments, the lamp may go from off to full brightness as desired. Further, at the alarm time one or more rendering devices (as a portion of the secondary device and/or separate from it) may for example vibrate and/or produce an auditory rendering.

Figure 6:
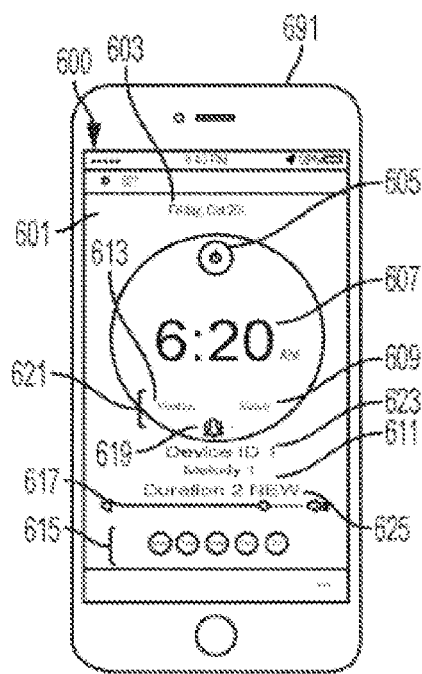
FIG. 6 shows a screen shot of portion of an alarm configuration graphical user interface (GUI) generated in accordance with embodiments of the present system.

The setup routine of the application may provide a user with a suitable interface such as a graphical user interface (GUI) with which a user may interact in accordance with the present system, such as for example to configure one or more of the primary and secondary devices. For example, the GUI may be utilized to set the alarm settings such as one or more alarm times for one or more corresponding alarm events. For example, FIG. 6 shows a screen shot 600 of a portion of an alarm configuration GUI 601 generated in accordance with embodiments of the present system. The GUI 601 may be rendered on any suitable device 691 such as a smart phone (e.g., an iPhone™ is illustratively shown), laptop, tablet and/or other device and the like. In accordance with embodiments of the present system, the GUI may be provided by an application, such as an app running on the device 691.

Referring to FIG. 6, the GUI 601 may include day/date information 603 that a user may select to set the day and/or date of a given alarm event (e.g., 3 P.M. on Monday, Wednesday and Friday, October 25, etc.). The GUI 601 may include a plurality of menu-items with which a user may select set and/or reset one or more alarm events. For example, a user may select the day/date information 603 (e.g., by selecting the day/date information 603 menu item) and the process upon determining that the user has selected day/date information may generate a text entry box and/or a calendar with which a user may enter information related to a selected day/date/year for a current alarm event. The current alarm event may be switched on or off using an alarm on/off icon 605 which may indicate whether the alarm is set to be activated (e.g., as illustrated by an "on" icon) or not activated (e.g., as may be illustrated by an "off" icon for example in place of the "on" icon) at the current alarm event time. For example, an "on" symbol may indicate that that the current event is an active event (e.g., in which an alarm signal is to be generated) while an "off" signal indicates that the current event is not an active event (e.g., is an inactive event in which an alarm signal will not be generated).

Alarm time information 607 may indicate a time at which current given indicated alarm event is to occur (e.g., an alarm time/date/condition setting). Alarm rendering information 621 may indicate whether vibration and/or sound modes (e.g., as represented by vibration and sound modes menu items 613 and 609, respectively) are to be used for rendering an alarm of the current alarm event as well as indicating desired rendering information (e.g., visual, auditory and/or haptic) and/or related devices (e.g., internal and/or external devices rendering devices), such as a desired melody for an auditory alarm to be produced by a given rendering device in an embodiment wherein different auditory rendering information and/or devices are selectable. A user may tap on visual, vibration and/or sound modes menu items, such as vibration and/or sound modes menu items 613 and 609, respectively, to toggle the mode on or off (e.g., bright=on, dim=off) as may be desired.

A selected melody (e.g., a sound file for rendering) for a sound mode may be illustrated using by a melody menu item 611 (e.g., Melody 1, 2, 3, . . . m–1, M, etc.). In accordance with embodiments of the present system, there may be one or more selected melodies (e.g., M, where M is an integer) which may be stored for example as prerecorded and/or otherwise generated sound files (e.g., default memories stored prior to delivery of the secondary device to the user) in a memory of the system such as a memory of the primary and/or secondary device. Accordingly, a user may not have to load rendering information, such as melodies as separate files. For example, in accordance with embodiments of the present system, a user may select melodies from a stored plurality of melodies available on the secondary device thus simplifying a method of setting alarms. The rendering information such as melodies may be identified by name (e.g., melody 1, melody 2, etc.), genre (e.g., Rock, Classical, etc.), and/or by description (e.g., for a melody, by title, author, singer, band, etc.). In accordance with embodiments of the present system, the melodies may include songs, repeating patterns (e.g., in pitch and/or tone), white noise, etc. In accordance with embodiments of the present system, the melodies may also be utilized for operating the haptic device so that in effect, the melody may in place of or in addition to being utilized for auditory rendering, may be utilized for generating haptic rendering, such as following a baseline of a selected melody.00

It is further envisioned that the primary device and the secondary device may communicate with each other, for example, to identify melodies stored in a memory of the secondary device. During this communication, the primary device and the secondary device may synchronize with each other so that information such as sound files of the secondary device may be discovered by the primary device. Similarly, files of the primary device such as sound files may be transmitted to the secondary device. Further, the secondary device may communicate with one or more external devices (e.g., other devices) for example to determine the rendering capabilities of the one or more external devices (e.g., auditory, haptic, etc.).

In accordance with embodiments of the present system, the secondary device may include melodies such as from a given genre which may be pre-programmed at the factory. Thus, a Rock-type secondary device may include rock-type melodies while a Classical-type secondary device may include classical-type melodies. A user may then select a secondary device based upon the type of music desired for the alarm. Graphics and/or color of a secondary device may be customized so as to identify a type of secondary device. In accordance with embodiments of the present system, the user may load and/or otherwise alter previously stored files such as the sound files (e.g., melodies) into the primary device and/or the secondary device.

Referring back to FIG. 6, a user may select a rendering mode/menu item, such as the melody menu item 611 (e.g., by swiping through an open or closed (e.g., a last melody of the list connects to a first item of the list) of available melodies, etc. The system may display a plurality of available melodies (e.g., sound files) which a user may select to associate with the current alarm event. Then, the system may set this user-selected melody (e.g., sound file) as a selected melody as may be represented by menu item 611 (e.g., "MELODY 1"). Thus, in a case wherein the user selects MELODY 5, the system may set this melody as the selected melody. In a case wherein the sound mode is selected (e.g., see, sound modes menu item 609), the secondary device may transfer the sound mode such as an alarm event to the secondary device for subsequent rendering of the selected melody (e.g., audibly and/or haptically, see act 519 discussed further herein) when the corresponding alarm event is triggered for example at a set alarm time and/or date. An alarm event number 619 may indicate a number (e.g., in consecutive order) of a current alarm event (e.g., "1" next to the alarm bell). In accordance with embodiments of the present system, there may be a plurality (e.g., X) of alarm events as discussed.

Figure 7:
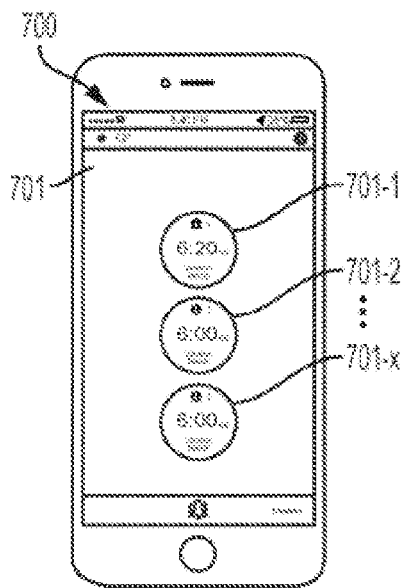
FIG. 7 shows a screen shot of a portion of an alarm configuration GUI generated in accordance with embodiments of the present system.

For example, FIG. 7 shows a screen shot 700 of a portion of an alarm configuration GUI 701 generated in accordance with embodiments of the present system. Assuming that there are X current alarm events (where X is an integer), each of these X current alarm events may be represented by an alarm event window 701-1 through 701-X (generally 701-*x*) as shown. A user may select any of these alarm event windows 701-*x* (e.g., by swiping, double clicking, etc., as may be set by default, by the user and/or by the system) and the system may then display more detailed information about the selected alarm event and/or may provide a user with an interface with which the use may interact to change settings of the corresponding alarm event. Thus, in a case wherein X=3, the three alarm event windows 701-1, 701-2, and 701-X may be rendered by the process for the convenience of the user. Further, each alarm event may have a predetermined alarm duration value associated with it (e.g., see, alarm duration 625, shown in FIG. 6 which in the illustrative embodiment is set to 2 min). This value may be set by default, by the system and/or by a user and may correspond to a total alarm rendering time as discussed herein.

Referring back to FIG. 6, the process may generate a volume menu item such as a volume slider 617 with which a user may interact to view and/or set/reset a volume of the corresponding selected melody (e.g., see 611 MELODY 1 in FIG. 6). Accordingly, a user may slide the volume slider 617 to set a volume of the selected melody to be associated with the current alarm event. Similarly, a haptic menu item such as a vibration slider may be generated so that a user may select a haptic force, frequency and/or pattern (e.g., vibrate, stop, vibrate, stop, etc.) to associate with a corresponding vibration mode to associate with the current alarm event (e.g., be haptically rendered by the current alarm event). Similarly, a visual (e.g., lighting) menu item may be generated so that a user may select a brightness levels, frequency and/or pattern (e.g., turn on brightness, start dim and brighten in intervals, etc.) to associate with a corresponding alarm event. In accordance with embodiments of the present system, a single slider, such as the slider 617 may be utilized to set two or more of a volume, a haptic force and a brightness associated (e.g., rendered) with a given melody and/or alarm event.

A weekday menu item 615 may indicate a day of week selected for a current alarm (e.g., 7 day alarm). For example, in a case wherein a user would like the current alarm event to be generated each week on the same day and/or time (e.g., every Friday at 6:20 A.M.), a user may select one of the days in the weekday menu item 615 so as to associate the selected day of the week with the current alarm event. In accordance with embodiments of the present system, a device ID 623 may identify a device associated with the current alarm event. Thus, in a case wherein a device by ID 1 is identified with the current alarm event, when the current alarm event is determined to occur (e.g., at its alarm time, date, etc.), the alarm may be rendered using a device whose identification is ID 1. The process may then store these alarm settings as alarm information in a memory of the system such as a memory of the primary device and/or secondary device.

In accordance with embodiments of the present system, the primary device and the one or more secondary devices may be coupled (e.g., through a network, etc.) to determine capabilities of the one or more secondary devices and/or to transmit information, such as alarm information, therebetween. For example, in accordance with embodiments of the present system some secondary devices may include sensors, switches, ports, etc., of different types than other secondary devices. For example, some secondary devices may include motion sensors (e.g., acceleration sensors, gravity sensors, etc.) while other secondary devices may not and/or may include one or more other sensors. Thus, the capabilities of secondary devices may differ as desired. For example, a basic secondary device may be provided that has less features and/or programmable capabilities than a higher end (e.g., more expensive) secondary device. Accordingly, a primary device may query a given secondary device to identify the capabilities of the given secondary device. Then, the primary device may take into account the capabilities of the secondary device to form settings, menus, GUIs, etc., which may correspond with the capabilities of a specific secondary device. Thus, for example, a given secondary device may include a temperature sensor. Accordingly, the primary device may detect this capability, acquire stored and/or current temperature information from the temperature sensor and provide a suitable interface (e.g., GUI) for this secondary device, such as provide a display of temperature information, enable operating modes, etc., for the convenience of a user. Similarly, a secondary device may include capabilities to operate as a remote speaker phone (e.g., microphone and/or speaker) in concert which a phone application of the primary device. Accordingly, in these embodiments, the primary device may be operative to control the secondary device to act as a speaker phone and/or otherwise provide a GUI for use, setting, etc., of this capability. As may be readily appreciated, in a case wherein a secondary device does not have a given capability, the present system may adapt the provided GUI to delete and/or otherwise indicate that a given capability is not supported by a given secondary device. In accordance with embodiments of the present system, portions of the operating mode such as alarm information may be transmitted to one or more memories (e.g., a memory present on the secondary device) for storage.

Referring back to FIG. 5, after completing act 513, the secondary device may receive the information sent by the primary device during act 517. As discussed, during act 517, the secondary device may receive the control information from the primary device and process this signal to extract the control information, such as alarm information contained therein. The extracted control information may include information which indicates whether to, for example, turn on or off a current alarm, whether to enable or disable sound (e.g., turn sound on or off, respectively), whether to turn a vibrator on or off, whether to play a sound file (e.g., a sound file that is identified by the sound file ID and which may be stored in a memory of the secondary device), whether to control an external device at the time of an alarm, and/or otherwise set an operating mode of the secondary device as discussed herein After completing act 517, the process may continue to act 518.

During act 518, the secondary device may process the control information such as form an alarm signal based upon alarm information extracted from the control information.

Accordingly, the secondary device may analyze the extracted alarm information and use this information to determine for example a response when rendering an alarm (e.g., see act 519). In accordance with embodiments, a secondary device may have available locally (e.g., in a memory such as the memory 1020 illustratively shown in FIG. 10) responses that are available to the secondary device (e.g., haptic, visual, auditory, etc.), though in accordance with embodiments of the present system, further responses may also be received for example as a portion of the alarm information. Based upon these determinations, the process may form the alarm signal at the secondary device. The alarm signal may include one or more continuous and/or discrete signals (e.g., stored, received, etc.) and may be transmitted to one or more corresponding rendering devices of the secondary device and/or separate from the secondary device which are determined to be operative or otherwise available (e.g., for a separate rendering device) when rendering the alarm. For example, in a case wherein it is determined to play a melody (e.g., stored and/or received such as from the primary device), the alarm signal may include this melody and, as such, may include audio information which may be transmitted to a rendering device such as a speaker when rendering the alarm. Further, the secondary device may determine that an external speaker is available, such as through a Bluetooth™ communication link and the audio information may be transmitted also or alternatively to the external speaker for rendering the alarm.

With regard to the haptic rendering device, such as a vibrator, in a case wherein it is determined to operate a vibrator, the alarm signal may include a signal which may cause the vibrator to operate when rendering the alarm. Accordingly, the alarm signal may include a signal to switch the vibrator on (e.g., toggle on) and/or may include a signal to drive the vibrator such that, after the end of the signal is rendered, the vibrator stops operating. In accordance with embodiments of the present system, this signal may be transmitted to the vibrator and may include a discrete signal (e.g., to toggle the vibrator on or off) or a constant signal (e.g., to drive the vibrator) when rendering the alarm.

Thus, in accordance with embodiments of the present system, the process may form one or more alarm signals configured to drive one or more rendering devices in accordance with the extracted alarm information. For example, in a case wherein the extracted alarm information requires vibration to be output but no melody to be played, the process may form an alarm signal to drive an internal vibrator of the secondary device and/or an external vibrator when rendering the alarm. During this act, in a case wherein a melody (e.g., sound file) is to be played during an alarm event, the process may obtain the corresponding sound file from a memory of the system such as a memory of the secondary device and may generate a corresponding alarm signal for example to drive the speaker. In this way, the melody may be rendered by the speaker. In accordance with embodiments of the present system, the sound file may be maintained locally. In this way, the process may for example conserve system resources by not having to stream the sound file from the primary device. After completing act 518, the process may continue to act 519.

During act 519, the secondary device may operate to set an operating mode such as to render the alarm signal at the time of a set alarm. Accordingly, the alarm signal may be provided to one or more rendering devices which may then render the alarm signal. During this act, the process may also start an alarm interval counter which may count a total time that the current alarm signal is being rendered by the secondary device and/or one or more other rendering devices.

In accordance with embodiments of the present system, when the secondary device is programmed to perform in accordance with an operating mode, one or more of the primary and secondary device may also communicate with one or more further devices (e.g., other devices) to control operation of the one or more other devices. For example, in a case wherein the secondary device is programmed to facilitate sleep of the user, such as by rendering a descending audio output, the secondary device may communicate with another device, such as a thermostat over a wireless coupling (e.g., Bluetooth™), to reduce a heat setting of the thermostat while controlling the internal and/or external rendering device. Similarly, in a case wherein the secondary device is programmed to facilitate waking of the user, such as by controlling a rendering device to render an ascending audio output, the secondary device may communicate with the other device at that time or some predetermined time before, to increase a heat setting of the thermostat, light setting of a lamp, etc. As readily appreciated, while external devices (e.g., one or more other devices) such as rendering devices, a thermostat, etc., are illustratively described as other devices, additional devices and device types may be suitably controlled.

In accordance with embodiments of the present system, the secondary device may attempt communication with the primary device at the alarm time. For example, at the alarm time the secondary device may though need not attempt to communicate with the primary device (e.g., such as over a Bluetooth™ connection) to determine whether the primary device is available. In accordance with embodiments of the present system, when the primary device is available (e.g., active, in a sleep state, etc.), the user interface may be produced on the primary device to facilitate operation, such as to control the alarm rendered during act 519 (e.g., see act 523 described below). As envisioned, whether or not the primary device is available when the alarm is rendered, stopped, etc., the secondary device will operate as described. After completing act 519, the process may continue to act 521.

During act 521 the process may determine whether an off and/or other control signal is generated. In accordance with embodiments of the present system, the off and/or other control signal may be generated at the secondary device directly, such as through operation of one or more of the buttons, switches, etc., present on the secondary device. In addition, the off and/or other control signal may be generated at the primary device (e.g., through operation of the application interface, such as the user interface provided by the application on the primary device) and be transmitted to the secondary device to directly control the secondary device when a communication link is present between the primary and secondary devices. For example, when an alarm event occurs on the secondary device, it may automatically search for a corresponding primary device, such as a smartphone. In a case wherein a corresponding smartphone for example is found, the secondary device may for example pair with the smartphone, bring up the corresponding user interface (e.g., application), etc., so that the operation of the secondary device may be controlled from the smartphone without requiring further intervention from the user (e.g., without requiring a manual pairing operation by the user). In this way, control of the secondary device may be performed directly on the primary device at the alarm time for example to make it easier to snooze/turn off the secondary device via the smartphone user interface. Accordingly, in a case wherein it is determined that the off and/or other control signal is generated, the process may continue to act 523 where it may respond accordingly. For example, the smartphone may be utilized to turn off the alarm by, for example, sending control information to the secondary device to terminate the alarm signal provided to the rendering device and/or other devices. Thereafter, the process may end during act 573.

However, in a case wherein it is determined that the off signal is not generated, the process may continue to act 525. During act 525, the process may determine whether a snooze signal is generated (e.g., in a case wherein a snooze switch is actuated) on the primary and/or secondary device as similarly described regarding the off signal. Accordingly, in a case wherein it is determined that a snooze signal is generated, the process may continue to act 527. However, in a case wherein it is determined that a snooze signal is not generated, the process may continue act 521 for example until an end alarm time interval is reached, an off switch is actuated or until a snooze button is actuated. For example, the alarm interval may be determined to elapse when an alarm interval counter has a value which is greater than or equal to a predetermined alarm duration value. The alarm duration value may be set to a value by default, by the system and/or by a user to represent a maximum alarm duration such as 120 seconds, etc. The alarm interval may be determined not to have elapsed when the alarm interval counter has a value which is less than the predetermined alarm duration value.

During act 527, the process may perform a snooze process using any suitable system. For example, the process may temporarily interrupt the current alarm (e.g., by interrupting the alarm signal) for a snooze period of time (e.g., 5 minutes, etc., as may be determined by default, by the system and/or by a user). Accordingly, the process may start a timer to determine when the snooze period of time elapses and may then resume the rendering of the alarm signal as before snoozing (e.g., see act 519). Further, it is envisioned that the process may suspend the alarm interval timer during the snooze period so that the alarm interval timer stops during the snooze period and starts (from the same count) when the snooze period of time elapses. After completing act 527, the process may repeat act 521. Accordingly, in a case wherein another command (e.g., snooze or off for one or more rendering devices) is received while already snoozing, the process may reset the snooze (e.g., start a new snooze interval) or turn off the one or more rendering devices as appropriate.

In accordance with embodiments of the present system, the snooze signal may be generated by selecting (e.g., by depressing, etc.) a snooze key (e.g., a snooze button, a user interface item, etc.) on the secondary device and/or on the primary device as described. Selection of the snooze key may generate a signal to inform the secondary device of the selection by, for example, transmitting the signal that the snooze key was selected to the secondary device. The secondary device in receipt of this signal may then take appropriate action. For example, the secondary device may temporarily interrupt the current alarm (as described above) for a threshold period of time as described above with respect to act 525. Similarly, the primary device when in communication with the secondary device during the alarm event may update a status of the corresponding alarm event, for example to indicate on the user interface that the secondary device was instructed to snooze and may render this updated status on a rendering device of the system, as desired. Accordingly, when a user selects (e.g., by depressing) a snooze button on the secondary device, the primary device may be informed of this and may render information indicating such (e.g., 5 min snooze on).

Figure 8:
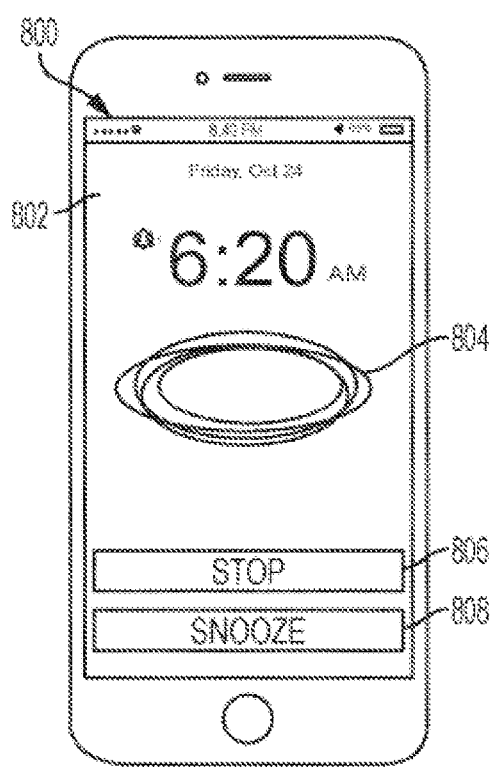
FIG. 8 shows a screen shot of a portion of an alarm configuration GUI generated in accordance with embodiments of the present system.

With regard to acts 519 and 523, the snooze and off buttons may be situated on the secondary device and/or primary device as described. For example, with regard to the primary device that is in communication with the secondary device when an alarm event occurs, the process may generate a GUI to indicate to a user a current status of the alarm event and on/off/snooze keys (e.g., user interface objects such as a display of selectable buttons provided on the UI) for a user to select. For example, FIG. 8 shows a screen shot 800 of a portion of an alarm configuration GUI 801 generated for example on a primary device in accordance with embodiments of the present system. A graphical representation 804 may illustrate a current status of the secondary device (e.g., vibrating). One or more menu items such as Stop and Snooze menu items, 806 and 808, respectively, may include menu-items generated in accordance with embodiments of the present system. The graphical representation 804 may be based upon the alarm information.

Figure 9:
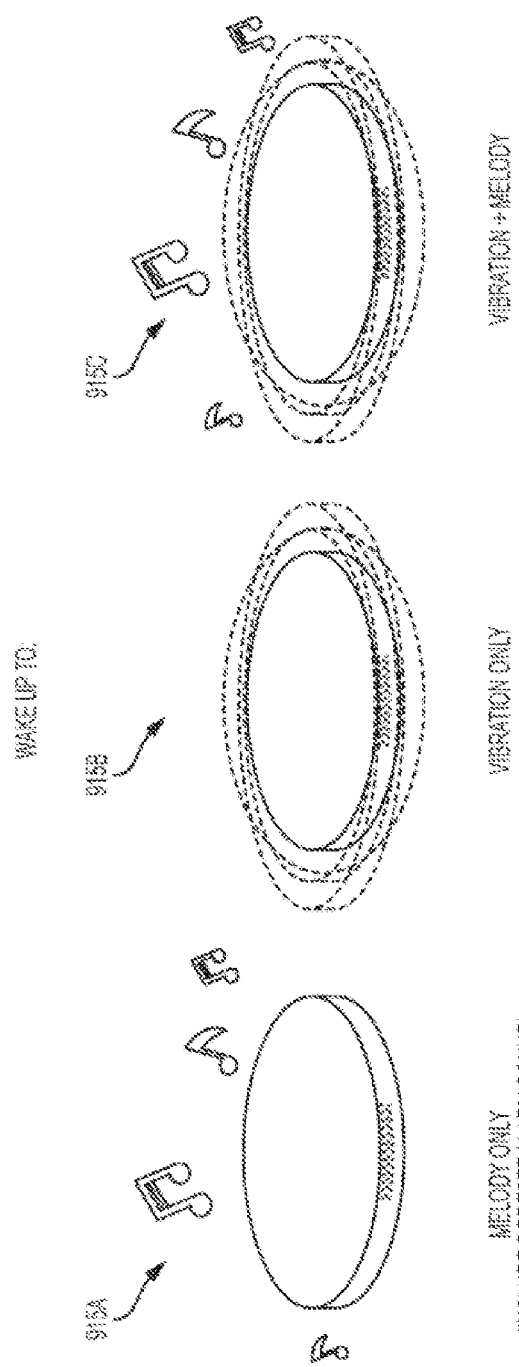
FIG. 9A shows a portion of a graphical representation that may be rendered in accordance with embodiments of the present system.
FIG. 9B shows a portion of a graphical representation that may be rendered in accordance with embodiments of the present system.
FIG. 9C shows a portion of a graphical representation that may be rendered in accordance with embodiments of the present system.

For example, FIG. 9A, FIG. 9B and FIG. 9C each show a portion of graphical representations 915A through 915C, respectively, that may be rendered in accordance with embodiments of the present system. For example, in a case wherein the alarm information is set for rendering an audible melody only, a melody only graphical representation as shown in FIG. 9A may be rendered on a primary device. Similarly, in a case wherein the alarm information is set to vibration only, a vibration only graphical representation of FIG. 9B may be rendered. Lastly, in a case wherein the alarm information is set to vibration and melody, a vibration and melody graphical representation may be rendered as shown in FIG. 9C. These representations may represent a current state of an alarm which is currently occurring on the secondary device and may be updated in real time and/or may represent a future state of a given alarm.

With regard to the snooze and/or off keys, in accordance with embodiments of the present system it is envisioned that one or more of these keys may be generated by moving the primary or secondary device in a desired pattern (e.g., a horizontal waving, etc.). In this way, movement sensors (e.g., accelerometers, motion sensors, etc.) may identify for example movement actions and then form corresponding alarm information. For example, the process may analyze the motion information to detect a corresponding motion. In a case wherein the corresponding motion is determined to match a predetermined pattern (e.g., where the patterns may be defined for each action such as an off pattern, a snooze pattern, etc. as may be defined by default, by the user and/or by the system), the process may take an appropriate action without further interaction with a corresponding user interface. For example, in accordance with embodiments of the present system, moving the primary or secondary device in a sideways pattern (e.g., laterally) may indicate a snooze command. Similarly, in accordance with embodiments of the present system, moving the primary or secondary device in an up and down pattern may indicate an off command. This motion may be sensed by one or more sensors of a corresponding device such as motion sensors and may be determined by a controller of the corresponding device or, for example in a case wherein the device is a secondary device, identified motion information may be communicated to the primary device for determination by a controller of the primary device. In this way, sensor data from the secondary device may be transmitted to the primary device in real time for analysis.

In accordance with embodiments of the present system, a user may shake or otherwise move the primary or secondary device in a desired pattern, the process may detect the desired pattern of motion (e.g., through an analysis of motion information from one or more sensors of the system), the process may then determine whether there is a command (or task) assigned to the detected pattern of motion, and in a case wherein it is determined that there is a command (or task) assigned to the detected pattern of motion, the process may perform this command or task.

Figure 10:
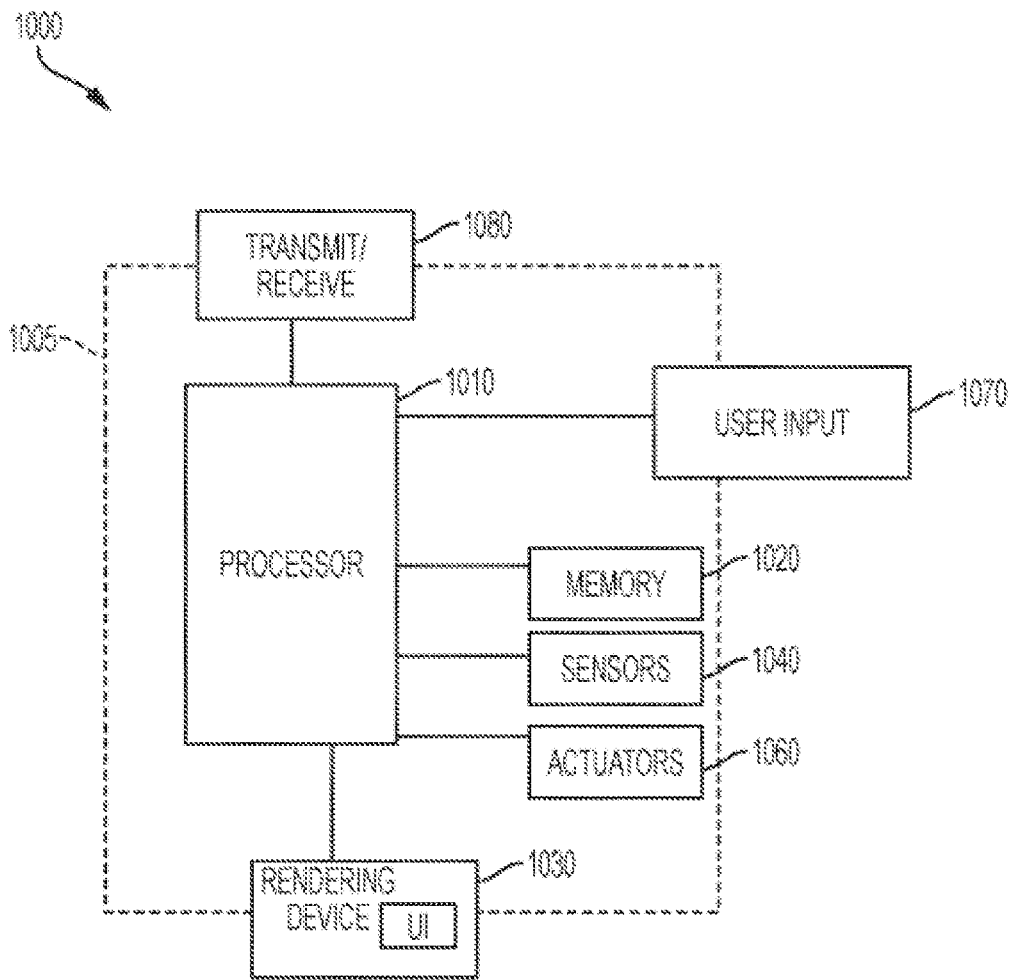
FIG. 10 shows a portion of a system in accordance with embodiments of the present system.

FIG. 10 shows a portion of a system 1000 including a secondary device 1005 in accordance with embodiments of the present system. For example, a portion of the present system may include a processor 1010 (e.g., a controller) operationally coupled to a memory 1020, one or more rendering devices 1030 such as a display, haptic device, etc., one or more sensors 1040, one or more actuators 1060, a transmit/receive (Tx/Rx) portion 1080, and a user input device 1070. In accordance with embodiments of the present system, although each of the memory, the rendering device, the one or more sensors, the one or more actuators 1060, and the transmit/receive (Tx/Rx) portion 1080 are shown separately for clarity, one or more of these portions may be combined together with the processor. For example, the processor may include the transmit/receive (Tx/Rx) portion. Further, the portions shown may also be encompassed by one or more discrete devices (e.g., separate from the secondary device 1005) such as portions of the rendering device 1030, the user input device 1070 and/or other devices as described herein. For example, while the user input 1070 may form a portion of the secondary device 1005 (e.g., snooze key, etc.), the user input may also or alternatively be a portion of the primary device as described. Further, the transmit/receive (Tx/Rx) portion may be made up of two or more discrete portions, such as a transmitter/receiver portion and a discrete antenna. In addition, the memory 1020 may be any type of device for storing application data as well as other data (e.g., auditory, visual and haptic responses to alarm information) related to the described operation. The application data and other data are received by the processor 1010 for configuring (e.g., programming) the processor 1010 to perform operation acts in accordance with the present system. The processor 1010 so configured becomes a special purpose machine particularly suited for performing in accordance with embodiments of the present system.

The user input 1070 may include a keyboard, a mouse, a trackball, a motion-sensitive device or other device, such as a touch-sensitive display, which may be stand alone or be a part of a system, such as part of a personal computer, a personal digital assistant (PDA), a mobile phone (e.g., a smart phone), a monitor, a wearable display (e.g., smart glasses, etc.), a smart- or dumb-terminal or other device for communicating with the processor 1010 via any operable link. The user input device 1070 may be operable for interacting with the processor 1010 including enabling interaction within a user interface (e.g., GUI) as described herein. Clearly the processor 1010, the memory 1020, the rendering device 1030, and/or user input device 1070 may all or partly be a portion of a computer system or other device such as a primary, secondary and/or other device as described herein.

The actuators 1060 may be controlled by the processor 1010 in accordance with embodiments of the present system. The actuators 1060 may control one or more haptic devices such as one or more vibrators, motors, etc., of the system so as to generate a desired vibration under the control of the processor 1010. For example, in accordance with embodiments of the present system, the actuators 1060 may include a motor controller which may control the speed of a vibrator under the control of the processor 1010. In accordance with embodiments of the present system, the actuators may be a portion of an external haptic device that may operate under control of the processor 1010 such as through a wireless link.

The methods of the present system are particularly suited to be carried out by a computer software program, such program containing modules corresponding to one or more of the individual steps or acts described and/or envisioned by the present system. Such program may of course be embodied in a computer-readable medium, such as an integrated chip, a peripheral device or memory, such as the memory 1020 or other memory coupled to the processor 1010.

The program and/or program portions contained in the memory 1020 may configure the processor 1010 to implement the methods, operational acts, and functions disclosed herein. The memories may be distributed, for example between the primary and/or secondary devices, or local, and the processor 1010, where additional processors may be provided, may also be distributed (e.g., as a portion of one or more of the primary device, the secondary device, the rendering device and/or other devices that operate in accordance with embodiments of the present system) or local to a device. The memories may be implemented as electrical, magnetic or optical memory, or any combination of these or other types of storage devices. Moreover, the term "memory" should be construed broadly enough to encompass any information able to be read from or written to an address in an addressable space accessible by the processor 1010. The memory 1020 may include a non-transitory memory. With this definition, information accessible through a network such as the network 1080 is still within the memory, for instance, because the processor 1010 may retrieve the information from the network 1080 for operation in accordance with the present system.

The processor 1010 is operable for providing control signals and/or performing operations in response to input signals from the user input device 1070 as well as in response to other devices of a network (e.g., in response to signals received from a primary device) and executing instructions stored in the memory 1020. The processor 1010 may include one or more of a microprocessor, an application-specific or general-use integrated circuit(s), a logic device, etc. Further, the processor 1010 may be a dedicated processor for performing in accordance with the present system or may be a general-purpose processor wherein only one of many functions operates for performing in accordance with the present system. The processor 1010 may operate utilizing a program portion, multiple program segments, or may be a hardware device utilizing a dedicated or multi-purpose integrated circuit.

While the present invention has been shown and described with reference to particular exemplary embodiments, it will be understood by those skilled in the art that present invention is not limited thereto, but that various changes in form and details, including the combination of various features and embodiments, may be made therein without departing from the spirit and scope of the invention.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. In addition, the section headings included herein are intended to facilitate a review but are not intended to limit the scope of the present system. Accordingly, the specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise;

h) no specific sequence of acts or steps is intended to be required unless specifically indicated;

i) the term "plurality of" an element includes two or more of the claimed element, and does not imply any particular range of number of elements; that is, a plurality of elements may be as few as two elements, and may include an immeasurable number of elements; and j) the term and/or and formatives thereof should be understood to mean that only one or more of the listed elements may need to be suitably present in the system in accordance with the claims recitation and in accordance with one or more embodiments of the present system.

The invention claimed is:

1. An alarm and monitoring system comprising a primary device and at least one secondary device, the alarm and monitoring system comprising:
    at least one controller configured to:
    determine whether at least one alarm event is set;
    establish a wireless communication between a primary device and the secondary device, when it is determined that the alarm event has been set;
    transmit an alarm event signal including alarm information from the primary device to the secondary device in accordance with the alarm event that is determined to have been set;
    generate an alarm signal by the secondary device in accordance with at least the alarm information; and
    render the generated alarm signal on a rendering device.

2. The alarm and monitoring system of claim 1, wherein the at least one controller is configured to receive the transmitted alarm event signal at the secondary device.

3. The alarm and monitoring system of claim 1, wherein the at least one controller is configured to generate the alarm signal at the secondary device.

4. The alarm and monitoring system of claim 1, wherein the at least one controller is configured to determine capabilities of the secondary device.

5. The alarm and monitoring system of claim 4, wherein the at least one controller is configured to form the alarm event signal in accordance with the determined capabilities of the secondary device.

6. The alarm and monitoring system of claim 5, wherein when generating the alarm signal, the at least one controller is configured to determine whether communication is established between the primary and secondary devices.

7. The alarm and monitoring system of claim 6, wherein when the at least one controller determines that communication is established, the at least one controller is configured to provide a user interface in accordance with the determined capabilities of the secondary device.

8. The alarm and monitoring system of claim 1, wherein the secondary device comprises a memory and the controller is configured to generate the alarm signal in accordance with rendering information that is stored in the memory.

9. The alarm and monitoring system of claim 1, wherein the secondary device is configured to control one or more other devices to generate the alarm signal.

10. The alarm and monitoring system of claim 9, wherein the one or more other devices comprises at least one of an auditory, visual and haptic rendering device to generate the alarm signal.

11. A method of operating an alarm and monitoring system comprising a primary device and at least one secondary device, the method comprising acts of:
    at least one controller
    determining whether at least one alarm event is set;
    establishing a communication between a primary device and the secondary device when it is determined that the alarm event has been set;
    transmitting an alarm event signal including alarm information from the primary device to the secondary device in accordance with the alarm event that is determined to have been set;
    generating an alarm signal by the secondary device in accordance with at least the alarm information; and
    rendering the generated alarm signal on a rendering device.

12. The method of claim 11, wherein the act of establishing the communication comprises an act of establishing a wireless communication between the primary and secondary devices.

13. The method of claim method 11, comprising an act of generating the alarm signal at the secondary device.

14. The method of claim 11, comprising an act of determining capabilities of the secondary device.

15. The method of claim 14, comprising an act of forming the alarm event signal in accordance with the determined capabilities of the secondary device.

16. The method of claim 15, wherein the act of generating the alarm signal comprises an act of determining whether communication is established between the primary and secondary devices.

17. The method of claim 16, wherein when it is determined that communication is established, the method comprising an act of providing a user interface in accordance with the determined capabilities of the secondary device.

18. The method of claim 11, the method comprising an act of generating the alarm signal in accordance with rendering information that is stored in a local memory.

19. The method of claim 11, comprising an act of controlling one or more other devices to generate the alarm signal.

20. The method of claim 19, comprising an act of the one or more other devices generating at least one of an auditory, visual and haptic alarm signal.

\* \* \* \* \*